(12) United States Patent
Elsasser et al.

(10) Patent No.: US 6,187,903 B1
(45) Date of Patent: Feb. 13, 2001

(54) METHOD OF PREPARING DIMERIC FATTY ACIDS AND/OR ESTERS THEREOF CONTAINING LOW RESIDUAL INTERESTERS AND THE RESULTING DIMERIC FATTY ACIDS AND/OR DIMERIC FATTY ESTERS

(75) Inventors: A. Fred Elsasser, Cincinatti, OH (US); Laura A. McCargar, Fort Thomas, KY (US)

(73) Assignee: Cognis Corporation, Gulph Mills, PA (US)

( * ) Notice: Under 35 U.S.C. 154(b), the term of this patent shall be extended for 0 days.

(21) Appl. No.: 09/363,459

(22) Filed: Jul. 29, 1999

(51) Int. Cl.$^7$ ............................ C07C 53/00; C07C 55/00; C09F 1/02; C09F 1/04; C11D 15/00
(52) U.S. Cl. .......................... 530/230; 530/223; 562/512; 562/512.4; 560/205; 585/365; 585/803
(58) Field of Search ..................................... 530/223, 230; 562/512, 512.4; 560/129, 205; 585/365, 803

(56) References Cited

U.S. PATENT DOCUMENTS

| | | |
|---|---|---|
| 2,793,219 | 5/1957 | Barrett et al. . |
| 2,793,220 | 5/1957 | Barrett et al. . |
| 2,955,121 | 10/1960 | Myers et al. . |
| 3,422,124 | 1/1969 | Milks et al. . |
| 3,632,822 | 1/1972 | Conroy . |
| 3,950,365 * | 4/1976 | Singer et al. .......................... 260/419 |
| 4,371,469 * | 2/1983 | Foglia et al. .......................... 554/161 |
| 4,776,983 | 10/1988 | Hayes . |
| 4,895,982 | 1/1990 | Pavlin et al. . |
| 5,001,260 | 3/1991 | Hayes . |

* cited by examiner

*Primary Examiner*—Nathan M. Nutter
(74) *Attorney, Agent, or Firm*—John E. Drach; Susan L. Hess

(57) ABSTRACT

A dimeric fatty acid and/or dimeric fatty ester product having a low residual content of interesters is obtained by hydrolyzing the interesters to provide monomeric unsaturated fatty acids and alcohols as the hydrolysates and thereafter removing the hydrolysates from the dimeric fatty acid and/or dimeric fatty ester product.

25 Claims, No Drawings

METHOD OF PREPARING DIMERIC FATTY ACIDS AND/OR ESTERS THEREOF CONTAINING LOW RESIDUAL INTERESTERS AND THE RESULTING DIMERIC FATTY ACIDS AND/OR DIMERIC FATTY ESTERS

BACKGROUND OF THE INVENTION

1. Field of the Invention

The present invention relates to a method of preparing dimeric fatty acids and/or esters thereof from unsaturated monomeric fatty acids and/or esters thereof. More particularly, the invention herein relates to a method of preparing dimeric fatty acids and/or esters thereof having a relatively low residual content of interesters, and to the dimeric fatty acid and/or dimeric fatty ester product which can be used to prepare higher molecular weight polymers than that obtained by polymerizing dimeric fatty acids and/or esters thereof with higher interester content.

2. Brief Description of the Prior Art

It is known that monomeric unsaturated fatty acids and the alkyl esters of these fatty acids can be utilized to manufacture dimeric fatty acids and dimeric fatty esters, which in turn, can be used to manufacture polyamide, epoxy and polyester resins for use, inter alia, in thermographic inks and coatings for plastic films, papers, and paperboard. Production of dimeric fatty acids and their esters typically comprises heating monomeric unsaturated monocarboxylic acids and/or their alkyl esters having from about 11 to about 24 carbon atoms, e.g., oleic acid, linoleic acid, esters of these fatty acids and the like, in the presence of a mineral clay and water, as described, e.g., in U.S. Pat. Nos. 3,632,822, 3,422,124, 2,793,219, 2,793,220, 2,955,121, and 4,776,983, the contents of each of which are incorporated by reference herein. A typical end product of these methods is a 36-carbon dicarboxylic dimeric fatty acid or ester thereof. Dimeric fatty acids can also be produced from dimerizing dicarboxylic acids and combinations of mono- and dicarboxylic acids as described, e.g., in U.S. Pat. Nos. 5,001,260 and 4,895,982, the contents of each of which are incorporated by reference herein.

Such methods of preparing dimeric fatty acids and dimeric fatty esters also result in the formation of one or more interesters, which result from the reaction of a double bond of an unsaturated fatty acid and ester thereof with water to form an alcohol which in turn reacts with a mole of acid to form interester. The presence of interesters in the dimeric fatty acid and fatty ester product has been found to hinder the formation of more desirable higher molecular weight polymers when the dimeric fatty acids and esters thereof are polymerized. Interesters cannot be readily removed from the dimeric fatty acids or their esters by simple methods, e.g., distillation, stripping, etc. Accordingly, an efficient, low cost method of preparing dimeric fatty acids or dimeric fatty esters of substantially reduced interester content is highly desired.

SUMMARY OF THE INVENTION

The present invention provides a method of preparing dimeric fatty acids and/or esters thereof having a low residual content of interesters. The method comprises:

a) dimerizing monomeric unsaturated fatty acids and/or esters thereof to provide a first mixture containing dimeric fatty acids and/or esters thereof, unreacted and/or rearranged monomeric fatty acids and/or esters thereof and interesters;

b) separating the unreacted and/or rearranged monomeric fatty acids and/or esters thereof from the first mixture to provide a second mixture containing dimeric fatty acids and/or esters thereof and interesters;

c) subjecting the second mixture to hydrolysis conditions to hydrolyze at least a portion of the interesters therein to monomeric fatty acids and alcohols thereby providing a third reaction mixture containing dimeric fatty acids and/or esters thereof, monomeric fatty acids and alcohols; and, d) separating monomeric fatty acids and alcohols from the third mixture to provide a dimeric fatty acid and/or dimeric fatty ester product having a reduced content of interesters relative to the interester content of the second mixture.

The foregoing method of preparing dimeric fatty acids and/or esters thereof results in the formation of a dimeric fatty acid and/or dimeric fatty ester product of reduced interester content. This product is especially useful for the manufacture of dimeric fatty acid and/or dimeric fatty ester polymers of relatively high molecular weights which cannot be obtained from dimeric fatty acids and/or esters thereof produced by known and conventional methods such as those referred to above.

As used herein, the term "unsaturated fatty acids" refers to monocarboxylic and/or polycarboxylic acids, e.g., dicarboxylic acids, having at least one double bond.

DESCRIPTION OF THE PREFERRED EMBODIMENTS OF THE INVENTION

The method of preparing dimeric fatty acids and/or fatty esters thereof having a low residual content of interesters as described herein can be utilized to dimerize any monomeric mono- or polyunsaturated fatty acid, esters of these fatty acids or mixtures thereof. Such monomeric unsaturated fatty acids and/or esters thereof can be obtained from an animal, vegetable, marine or synthetic source and typically have a chain length of from about 11 to about 24 carbon atoms. Suitable monounsaturated fatty acids and esters thereof include, but are not limited to, monounsaturated monocarboxylic acids such as oleic acid, elaidic acid and palmitoleic acid, monounsaturated polycarboxylic acids including dicarboxylic acids such as hexadec-8-enedioic acid, octadec-9-enedioic acid and 7-vinyl-tetradecanedioic acid, methyl, ethyl and other esters of the aforementioned fatty acids and mixtures thereof. Suitable polyunsaturated fatty acids and esters thereof include, but are not limited to, polyunsaturated monocarboxylic acids such as linoleic acid and linolenic acid and polyunsaturated polycarboxylic acids including dicarboxylic acids such as eicose-8,12-dienedioic acid, 8-vinyl-octadec-10-enedioic acid and 8,13-dimethyleicose-8,12,-dienedioic acid, methyl, ethyl and other esters of the aforementioned fatty acids and mixtures thereof. Suitable mixtures of both monounsaturated and polyunsaturated fatty acids and esters thereof include tall oil fatty acids, soybean fatty acids, corn oil fatty acids, canola fatty acids, cottonseed oil fatty acids, tallow fatty acids, rapeseed oil fatty acids, fish oil fatty acids and methyl, ethyl and other esters of the aforementioned fatty acids. This method can also be practiced on various mixtures of unsaturated fatty acids and/or esters thereof which also contain saturated fatty acids and/or esters thereof. For example, commercial oleic acid of high quality includes a minor amount, e.g., from about 5 to about 10 weight percent, of saturated fatty acids such as stearic and palmitic acids. The saturated fatty acids are not dimerized and are separated together with unreacted and/or rearranged monomeric unsaturated fatty acids. The rearranged monomeric fatty acids are formed during dimerization from rearrangement of the substrate monomeric unsaturated fatty acids utilized in dimerization. For example, oleic acid utilized as the substrate monomeric unsaturated fatty acid can rearrange during dimerization to form isostearic acid.

The method of preparing dimeric fatty acids or esters thereof initially involves dimerizing monomeric unsaturated fatty acids and/or esters thereof to provide a first mixture containing dimeric fatty acids and/or esters thereof, unreacted monomeric fatty acids and/or rearranged monomeric fatty acids and/or esters thereof and interesters. Methods of dimerizing fatty acids and/or esters thereof are well known in the art as described, e.g., in aforesaid U.S. Pat. Nos. 4,776,983, 3,422,124, 2,793,219, 2,793,220, 2,955,121, 3,632,822, 5,001,260 and 4,895,982. The dimerization of fatty acids and/or esters thereof typically involves charging a reaction vessel with unsaturated fatty acid and/or an ester thereof, e.g., oleic acid and methyl oleate, and heating the fatty acid and/or ester thereof at an elevated temperature, e.g., from about 230 to about 270° C., under autogenous pressure, e.g., from about 70 to about 175 psi, in the presence of a mineral clay, and preferably water and an alkali or alkaline earth metal salt, e.g., a lithium salt such as lithium carbonate.

The reaction vessel is equipped with an agitator to maintain the solids in suspension. In addition, the reaction vessel is kept sealed and is constructed in a manner to withstand the steam pressure generated at the temperature utilized. Exemplary of such reaction vessels are rocking autoclaves and autoclaves equipped with a stirring mechanism. The first mixture is typically heated for about 1 to about 6 hours until most of the monomeric unsaturated fatty acids and/or esters thereof have dimerized and the yield of dimeric fatty acids and/or esters thereof in the first mixture is from about 50 to about 60 weight percent.

The clay serves as a catalyst for promoting dimerization of the monomeric unsaturated fatty acids and/or esters thereof. Suitable clays include natural clays which are commercially available. The natural clays include, but are not limited to, hectorite, montmorillonite, attapulgite, halloysite, kaolinite, sepiolite, bentonite, and mixtures thereof. Preferably, the natural clay is calcium bentonite. Exemplary of a natural clay is Code 2 clay manufactured by Unimin Corp., Aberdeen, Miss. The amount of clay employed in the dimerization step depends on the nature of the clay to be utilized. Typically, the amount of clay ranges from about 1 to about 20 weight percent of the charged monomeric unsaturated fatty acids and/or esters thereof and is preferably from about 3 to about 7 weight percent of the charged monomeric unsaturated fatty acids and/or esters thereof.

The amount of water utilized in dimerizing the monomeric unsaturated fatty acids is preferably not greater than about 2 weight percent of the fatty acids and/or esters thereof.

As stated above, an alkali or alkaline earth metal salt may be employed in the dimerization step. Exemplary of such alkali or alkaline earth metal salts are lithium carbonate, lithium hydroxide, or other lithium salts. Preferably, the lithium salt is lithium carbonate. The amount of alkali or alkaline earth metal salt employed typically ranges from about 1 to about 7 weight percent of the clay used.

In a preferred dimerization operation, unsaturated fatty acids and/or esters thereof are heated at a temperature of about 250° C. at a pressure of from about 70 to about 175 psi in an autoclave for about 2 to about 6 hours in the presence of from about 2 to about 8 weight percent clay, and from about 0.05 to about 0.2 weight percent lithium carbonate to provide a first mixture containing dimeric fatty acids and/or esters thereof, unreacted and/or rearranged monomeric fatty acids and/or esters thereof and interesters. The first mixture may also contain polymeric fatty acids and/or esters thereof, e.g., trimeric fatty acid or trimeric fatty ester.

After heating is completed, the first mixture is cooled and is generally treated with acid, which forms salts with metals of fatty acid and fatty ester soaps that are formed during dimerization, which salts are either not soluble in the fatty acids and/or esters thereof or are absorbed onto the dimerization clay. Suitable acids include phosphoric acid, oxalic acid, citric acid, or sulfuric acid, with phosphoric acid being preferred. Following acid treatment, the first mixture is typically filtered to remove the clay and the insoluble salts.

After filtration, unreacted and/or rearranged monomeric fatty acids and/or esters thereof are separated from the first mixture to provide a second mixture containing dimeric fatty acids and/or esters thereof, interesters, polymeric fatty acids and/or esters thereof, and residual monomeric fatty acids and/or esters thereof. This is preferably accomplished by vacuum distillation, in the presence or absence of steam. Generally, the first mixture is fed into a still wherein the monomeric fatty acids and/or esters thereof are vaporized and separated as distillate while the dimeric fatty acids and/or esters thereof, interesters and polymeric fatty acids and/or esters thereof, referred to herein as the second mixture, are collected as residue from the base of the still. Generally, distillation is conducted at a temperature of from about 260 to about 320° C., and preferably at from about 260 to about 290° C., and at a pressure of from about 2 to about 10 Torr, and preferably from about 2 to about 6 Torr. The content of interesters in the second mixture typically ranges from about 0.8 to about 2.0 weight percent.

In the event that a significant amount of unreacted and/or rearranged monomeric fatty acids and/or esters thereof remain in the second mixture such fatty acids/esters can be further separated therefrom by, e.g., conducting another distillation step, prior to subjecting the second mixture to hydrolysis as hereinafter described. For example, the second mixture can be introduced into a wiped film still wherein unreacted and/or rearranged monomeric fatty acids and/or esters thereof are vaporized and separated as distillate. The residue containing dimeric fatty acids and/or esters thereof, interesters and polymeric acids and/or esters thereof, still referred to herein as the second mixture but of further reduced unreacted and/or rearranged monomeric fatty acid and/or ester content, is collected at the base of the still. This distillation step can be carried out at a temperature of from about 220 to about 260° C., and at a pressure of about 100 to about 300 microns. If desired, polymeric fatty acids and their esters which may be present in the second mixture can be separated therefrom, e.g., by distillation carried out at a temperature of from about 280 to about 320° C. and at a pressure of from about 100 to about 200 microns, to provide a distillate containing dimeric fatty acids and/or esters thereof, still referred to herein as the second mixture but of further reduced polymeric fatty acid or fatty ester content.

The second mixture is subjected to hydrolysis to hydrolyze at least a portion of the interesters therein to monomeric fatty acids and alcohols thereby providing what is referred to herein as the third mixture. This third mixture contains dimeric fatty acids and/or esters thereof, polymeric fatty acids and/or esters thereof and the foregoing hydrolyzed products, i.e., monomeric fatty acids and alcohols. Hydrolysis conditions include heating the second mixture to a temperature of from about 180 to about 250° C., and preferably at a temperature of from about 190 to about 205° C., under autogenous, atmospheric, nitrogen or hydrogen induced pressure, and preferably at a pressure of not greater than about 20 psi, in the presence of water and an acid-treated clay, for from about 1 to about 4 hours, and preferably from about 1 to about 2 hours. The resulting monomeric fatty acids and alcohol hydrolysates can be readily separated from the third mixture as described below.

The acid-treated clays which are preferably utilized for the hydrolysis of the interesters are the same clays as those that can be utilized in the dimerization step as described above, except that the clays have been treated with acid, e.g., sulfuric or hydrochloric acid. Preferably, the acid-treated clay is acid-leached bentonite. Exemplary of commercially available acid-treated clays are "Engelhard Grade F-20" and "F-13 Fitrol Clay" manufactured by Engelhard Industries, Jackson, Miss. The amount of clay utilized to hydrolyze interesters in the second mixture can typically range from about 0.5 to about 4 weight percent, and preferably from about 0.5 to about 1 weight percent, of the second mixture.

Following the hydrolysis operation which provides the third mixture, the latter is cooled and filtered to remove clay present. A filtering agent, e.g., "Dicalite 476" commercially available from Grefco, Inc., Cincinnati, Ohio, can be added to facilitate this filtration. Monomeric fatty acids and alcohols are then separated from the third mixture employing conventional procedures, e.g., vacuum distillation. Typically, the third mixture can be distilled in two stages using wiped film stills. In the first stage, the mixture is introduced into a wiped film still. Monomeric fatty acids and alcohols present in the third mixture are vaporized and collected as distillate and dimeric fatty acids and/or esters thereof of reduced interester content (relative to the interester content of the second mixture) and polymeric fatty acids and/or esters thereof are collected as residue from the base of the still. Generally, the first stage of distillation is conducted at a temperature of from about 230 to about 270° C., and preferably at a temperature of from about 260 to about 270° C., and at a pressure of from about 250 to about 1400 microns, and preferably from about 1000 to about 1200 microns. In the second stage, the residue is introduced into a wiped film still wherein the dimeric fatty acids and/or esters thereof are vaporized and collected as distillate while polymeric fatty acids and/or esters thereof remain in the residue. The second stage distillation is generally conducted at a temperature of from about 280 to about 300° C. and at a pressure of from about 65 to about 450 microns. The dimeric fatty acid and/or dimeric fatty ester product collected as distillate contains dimeric fatty acids and/or esters thereof having a much reduced content of interester. Typically, the interester content of the dimeric fatty acid and/or dimeric fatty ester product herein is not greater than about 0.2 weight percent, and preferably not greater than about 0.05 weight percent.

The dimeric fatty acid and/or dimeric fatty ester product herein is a useful starting material for other commercially important processes which are well known to those skilled in the art, e.g., hydrogenation in the presence of a catalyst, e.g., palladium on carbon catalyst, to provide a saturated dimeric fatty acid and/or dimeric fatty ester product, and polymerization, e.g., to provide polyamide resins.

Another aspect of the present invention lies in polymerizing the dimeric fatty acids and/or esters thereof of this invention with its reduced interester content to provide useful polymers, in particular, those having weight average molecular weights (Mw) significantly higher, e.g., at least about 2 percent higher and preferably at least about 4 percent higher, than polymers obtained by polymerizing dimeric fatty acids and/or esters thereof of relatively high interester content. Methods of polymerizing dimeric acids to form various products such as thermoplastic polyamides and resins thereof are described, e.g., in U.S. Pat. Nos. 4,760,125, 4,777,238, and 5,138,027, the contents of each of which are incorporated by reference herein.

The following examples are meant to illustrate but not to limit the invention.

EXAMPLE 1

Oleic acid obtained from tallow or vegetable oils, 4.4 weight percent Code 2 clay (Unimin Corp., Aberdeen, Miss.) and 0.09 weight percent lithium carbonate were heated to 250° C. at a pressure of 140–175 psi in an autoclave for four hours to provide a first mixture containing dimeric fatty acids, polymeric fatty acids, unreacted and/or rearranged monomeric fatty acids and interesters. The first mixture was then cooled to 135° C., treated with 0.9 weight percent 75% phosphoric acid and filtered to remove the inorganic salts, clay and phosphoric acid. Separation of unreacted and/or rearranged monomeric fatty acids from dimeric fatty acids and interesters in the filtered first mixture was accomplished by vacuum distillation in a still at a temperature of 275° C. and a pressure of 6 Torr. The distillate contained unreacted and/or rearranged monomeric fatty acids and the residue, i.e., the second mixture, contained dimeric fatty acids, interesters and polymeric fatty acids. The interester content of the second mixture as determined by proton nuclear magnetic resonance (NMR) using a Varian Unity 400 NMR (Varian, Inc., Palo Alto, Calif.) was found to be about 1.4 weight percent.

The second mixture to which was added 1 weight percent Engelhard Grade F-20 Filtrol Clay (Engelhard Industries, Jackson, Miss.) was stirred and heated in an autoclave at 200° C. at a pressure of 15 psi for 2 hours to effect hydrolysis of interesters. The resulting third mixture containing dimeric fatty acids and hydrolyzed product, i.e., monomeric fatty acids and alcohols, was cooled and filtered in the presence of 0.1 weight percent Dicalite 476 (Grefco, Inc., Cincinnati, Ohio) to remove the clay. The monomeric fatty acids and alcohols in the third mixture were separated therefrom by vacuum distillation on a wiped film still at a temperature of 250° C., and a pressure of 250 microns to yield a distillate containing monomeric fatty acids and alcohols, and a residue made up of dimeric fatty acids having a much lower interester content compared with that of the second mixture. The residue, which also contained polymeric fatty acids, was subjected to vacuum distillation at a temperature of 300° C., and at a pressure of 100 microns to yield a second distillate, containing 92.3 weight percent dimeric fatty acid product as determined by high pressure liquid chromatography and a residue containing most of the polymeric fatty acids. The dimeric fatty acid product was hydrogenated with 5 weight percent palladium on carbon to yield a hydrogenated dimeric fatty acid product. The yield of dimeric fatty acids in the final hydrogenated product was 93.9 weight percent. The total ester content of the final hydrogenated dimeric fatty acid product was determined by proton NMR (Varian Unity 400 NMR, Varian, Inc., Palo Alto, Calif.). The results are set forth in the Table, below.

TABLE

| TEST | ESTERS IN DIMERIC FATTY ACID PRODUCT | PERCENT ESTER IN DIMERIC FATTY ACID PRODUCT |
|---|---|---|
| NMR | METHYL ESTERS | 0.3 |
|  | ETHYL ESTERS | 0.004 |
|  | INTER ESTERS | <0.05 |
|  | WAX ESTERS | 0.1 |

As shown in the Table, the interester content of the final hydrogenated dimeric fatty acid product was not greater than about 0.05 weight percent.

EXAMPLE 2

This example also illustrates the present method as shown in Example 1, except the residue, i.e., second mixture containing dimeric fatty acids and interesters obtained from the first distillation step in Example 1, undergoes an additional two stage distillation procedure prior to the hydrolysis of interesters with acid-activated clay, to remove significant amounts of unreacted and/or rearranged monomeric fatty acids and polymeric fatty acids. The clay-treated mixture then is subjected to hydrogenation prior to the final distillation.

Oleic acid was dimerized as in Example 1, and the resulting first mixture was distilled to separate unreacted and/or rearranged monomeric fatty acids from dimeric fatty acids and interesters present in the first mixture as set forth in Example 1.

The residue from the distillation was then distilled in two stages using a wiped film still. Specifically, the residue was fed into a wiped film still and distilled at a temperature of 250° C. and at a pressure of 250 microns to remove a significant amount of the unreacted and/or rearranged monomeric fatty acids as distillate. The residue obtained from the first stage was then fed through a wiped film still and distilled at a temperature of 290° C. and at a pressure of 100 microns to form a second distillate containing dimeric fatty acids and interesters, and a residue containing polymeric fatty acids.

The second distillate, i.e., second mixture, and 1 weight percent Engelhard Grade F-20 Filtrol Clay (Engelhard Industries, Jackson, Miss.) were stirred and heated in an autoclave at 200° C. at a pressure of 15 psi for 1 hour to provide a third mixture which was then cooled and filtered in the presence of 0.1 weight percent Dicalite 476 (Grefco, Inc., Cincinnati, Ohio) to remove the clay. The filtered third mixture was then hydrogenated using 0.5 weight percent 5% palladium on carbon catalyst.

Monomeric fatty acids and alcohols were separated from dimeric fatty acids present in the hydrogenated third mixture by vacuum distillation on a wiped film still at a temperature of 250° C., and a pressure of 250 microns to yield a distillate containing monomeric fatty acids and alcohols, and a residue containing dimeric fatty acids and polymeric fatty acids. The residue was then fed into a wiped film still and distilled at a temperature of 290° C., and at a pressure of 100 microns to yield a distillate, i.e., dimeric fatty acid product, containing 92 weight percent dimeric fatty acids having an interester content of not greater than about 0.1 weight percent as determined by proton NMR (Varian Unity 400 NMR, Varian, Inc., Palo Alto, Calif.), and a residue containing mostly polymeric fatty acids.

EXAMPLE 3

This example is a modification of the procedure shown in Example 2, the modification being that hydrogenation occurs prior to the hydrolysis of interesters with acid-treated clay.

Oleic acid was dimerized and the resulting first mixture was distilled using the procedure as set forth in Example 1. The residue obtained from the first distillation was then distilled in two stages using wiped film stills, as set forth in Example 2.

The distillate obtained from the second stage of the second distillation, i.e., the second mixture which contained dimeric fatty acids and interesters, was hydrogenated with 5 percent palladium on carbon catalyst. The hydrogenated second mixture and 1 weight percent Engelhard Grade F-20 Filtrol Clay (Engelhard Industries, Jackson, Miss.) were stirred and heated in an autoclave at 200° C. at a pressure of 15 psi for 1 hour to provide a third mixture which was cooled and filtered in the presence of 0.1 weight percent Dicalite 476 (Grefco, Inc., Cincinnati, Ohio) to remove the clay and catalyst.

Monomeric fatty acids and alcohols produced from hydrolysis of interesters were separated from dimeric fatty acids present in the filtered clay-treated third mixture by vacuum distillation on a wiped film still at a temperature of 290° C. and a pressure of 300 microns to yield a distillate containing monomeric fatty acids and alcohols and a residue containing dimeric fatty acids and polymeric fatty acids. The residue was then fed into a wiped film still and distilled at a temperature of 320° C., and at a pressure of 200 microns to yield a distillate comprising 96 weight percent dimeric fatty acids having an interester content of not greater than 0.1 weight percent as determined by proton NMR (Varian Unity 400 NMR, Varian, Inc., Palo Alto, Calif.).

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

We claim:

1. A method of preparing dimeric fatty acids and/or esters thereof having a low residual content of interesters comprising:

a) dimerizing monomeric unsaturated fatty acids and/or esters thereof to provide a first mixture containing dimeric fatty acids and/or esters thereof, unreacted and/or rearranged monomeric fatty acids and/or esters thereof and interesters;

b) separating the unreacted and/or rearranged monomeric fatty acids and/or esters thereof from the first mixture to provide a second mixture containing dimeric fatty acids and/or esters thereof and interesters;

c) subjecting the second mixture to hydrolysis conditions to hydrolyze at least a portion of the interesters therein to monomeric fatty acids and alcohols thereby providing a third mixture containing dimeric fatty acids and/or esters thereof, monomeric fatty acids and alcohols; and d) separating monomeric fatty acids and alcohols from the third mixture to provide a dimeric fatty acid and/or dimeric fatty ester product having a reduced content of interesters relative to the interester content of the second mixture.

2. The method of claim 1 wherein the monomeric unsaturated fatty acids and/or esters thereof are selected from the group consisting of monounsaturated fatty acids, polyunsaturated fatty acids, esters thereof and mixtures thereof.

3. The method of claim 2 wherein the mixtures of monounsaturated and polyunsaturated fatty acids and esters thereof are selected from the group consisting of tall oil fatty acids, soybean fatty acids, corn oil fatty acids, canola fatty acids, cottonseed oil fatty acids, tallow fatty acids, rapeseed oil fatty acids, fish oil fatty acids and esters thereof.

4. The method of claim 2 wherein the monounsaturated and polyunsaturated fatty acids and/or esters thereof are selected from the group consisting of monocarboxylic acids, polycarboxylic acids, esters thereof and mixtures thereof.

5. The method of claim 1 wherein the polycarboxylic acids and/or esters thereof are dicarboxylic acids and esters thereof.

6. The method of claim 1 wherein dimerizing step (a) comprises heating the monomeric unsaturated fatty acids and/or esters thereof at a temperature of from about 230 to about 270° C. at a pressure of from about 70 to about 175 psi in the presence of a clay, an alkali metal salt or alkaline earth metal salt and water.

7. The method of claim 6 wherein the clay is calcium bentonite.

8. The method of claim 6 wherein the alkali earth metal salt is a lithium salt.

9. The method of claim 8 wherein the lithium salt is lithium carbonate.

10. The method of claim 6 wherein the water is present in an amount of not greater than about 2 weight percent of the fatty acids and/or esters thereof.

11. The method of claim 1 wherein the unreacted and/or rearranged monomeric fatty acids and/or esters thereof are separated from the first mixture by vacuum distillation.

12. The method of claim 11 wherein the vacuum distillation is conducted at a temperature of from about 260 to about 320° C. and at a pressure of from about 2 to about 10 Torr.

13. The method of claim 1 wherein the hydrolysis conditions comprise heating the second mixture at a temperature of from about 180 to about 250° C. under autogenous, atmospheric, nitrogen or hydrogen induced pressure in the presence of an acid-treated clay.

14. The method of claim 13 wherein the temperature is from about 190 to about 205° C.

15. The method of claim 13 wherein the pressure is not greater than about 20 psi.

16. The method of claim 13 wherein the acid-treated mineral clay is bentonite.

17. The method of claim 13 wherein the acid-treated clay is present in an amount of from about 0.5 to about 4 weight percent of the second mixture.

18. The method of claim 1 wherein the dimeric fatty acids and/or esters thereof are separated from the third mixture by vacuum distillation.

19. The method of claim 1 wherein the interester content of the dimeric fatty acid and/or dimeric fatty ester product is not greater than about 0.2 weight percent.

20. The method of claim 19 wherein the interester content of the dimeric fatty acid and/or dimeric fatty ester product is not greater than about 0.05 weight percent.

21. A dimeric fatty acid and/or dimeric fatty ester product produced according to the method of claim 1.

22. The dimeric fatty acid and/or dimeric fatty ester product of claim 21 having an interester content of not greater than about 0.2 weight percent.

23. The dimeric fatty acid and/or dimeric fatty ester product of claim 22 having an interester content of not greater than about 0.05 weight percent.

24. A dimeric fatty acid and/or dimeric fatty ester product having an interester content of not greater than about 0.2 weight percent.

25. The dimeric fatty acid and/or dimeric fatty ester product of claim 24 having an interester content of not greater than about 0.05 weight percent.

* * * * *